(12) United States Patent
Qian et al.

(10) Patent No.: US 7,639,848 B2
(45) Date of Patent: Dec. 29, 2009

(54) LESION MARKING AND CHARACTERIZATION QUALITY ASSURANCE METHOD AND SYSTEM

(75) Inventors: Jian-Zhong Qian, Princeton Junction, NJ (US); Guo-Qing Wei, Plainsboro, NJ (US); Li Fan, Belle Mead, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 695 days.

(21) Appl. No.: 11/105,957

(22) Filed: Apr. 14, 2005

(65) Prior Publication Data

US 2005/0251014 A1 Nov. 10, 2005

Related U.S. Application Data

(60) Provisional application No. 60/561,893, filed on Apr. 14, 2004.

(51) Int. Cl.
*G06K 9/00* (2006.01)
*G01N 35/00* (2006.01)

(52) U.S. Cl. .................................. 382/128; 436/43
(58) Field of Classification Search .......... 382/128–132
See application file for complete search history.

(56) References Cited

U.S. PATENT DOCUMENTS

| | | | |
|---|---|---|---|
| 5,933,519 A * | 8/1999 | Lee et al. | 382/133 |
| 7,295,691 B2 | 11/2007 | Uppaluri et al. | |
| 2003/0033090 A1* | 2/2003 | Callaway et al. | 702/19 |
| 2003/0095697 A1* | 5/2003 | Wood et al. | 382/131 |
| 2003/0165262 A1 | 9/2003 | Nishikawa et al. | |

* cited by examiner

*Primary Examiner*—Bhavesh M Mehta
*Assistant Examiner*—Hadi Akhavannik
(74) *Attorney, Agent, or Firm*—McDermott Will & Emery LLP (57) ABSTRACT

Method and system for quality assurance in lesion marking is disclosed. A marking is created based on a patient study on display in a manner in accordance with an electronically enforced protocol. One or more features are generated based on the marking. Quality of the marking is assessed based on such computed one or features.

53 Claims, 8 Drawing Sheets

LESION MARKING AND CHARACTERIZATION QUALITY ASSURANCE METHOD AND SYSTEM

The present invention claims priority of provisional patent application No. 60/561,893 filed Apr. 14, 2004, the contents of which are incorporated herein in their entirety.

BACKGROUND OF THE INVENTION

1. Field of the Invention

The present invention relates generally to a system and method for computer assisted medical diagnosis. Specifically, the present invention relates to a method and system for lesion detection procedures in diagnostic imaging.

2. Description of Related Art

A number of areas in diagnostic imaging have advanced rapidly, which makes a large amount of data readily available to medical personnel. However, advantages from these technological advancements also lead to new problems. For example, CT based cancer screening has progressed significantly. Different CT procedures enable large amount of data to be generated, which usually require tremendous effort from radiologists to examine such data to reach medical conclusions. To improve efficiency in processing such information, certain protocols governing medical data interpretation have been put in place. Although such protocols may assist radiologists to perform data interpretation in a more structured manner, performance of radiologists often varies significantly due to the amount of data. Such inconsistency complicates diagnostic decision making.

Second, various lesion/cancer databases have been established to encourage information exchange and sharing. One important application of such databases is to develop, test, and validate computer algorithms designed to detect and characterize different types of lesion/cancer. Effective use of such cancer databases often requires the availability of ground truth for lesion/cancer present in medical images and such ground truth is preferably validated by other means such as biopsies. However, due to the high cost of and extreme difficulty in acquiring ground truth, approximate ground truth is often used, which may be generated using lesion/cancer marks manually created by physicians. Unfortunately, establishing consistent lesion/cancer marks has proven to be very difficult. This is due to the fact that lesion/cancer markings of a patient study created by a radiologist at different times or by different radiologists often exhibit considerable variations. The former is called intra-observer inconsistency and the latter is called inter-observer inconsistency.

Generating consistent lesion/cancer markings has become a critical problem in diagnostic imaging and analysis. Recent research shows that markings created by radiologists at an expert level often have the same problem. Although this problem has attracted much attention, no effective solution has been proposed that adequately addresses the problem.

BRIEF DESCRIPTION OF THE DRAWINGS

The invention claimed and/or described herein is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

The present invention relates to a method and system for quality assurance in lesion marking and characterization. A method and system are disclosed herein for lesion marking with reduced intra and inter-observer inconsistencies. A lesion marking protocol is electronically enforced during the process of creating a lesion marking. Multiple markings created with respect to a lesion may be utilized to allow creation of a consensus lesion marking. Measures of intra-observer and inter-observer inconsistencies are estimated with respect to markings created for the same lesion. Such measures are used for quality assessment and assurance purposes. Information associated with lesion markings and creation thereof can be analyzed to derive statistics and knowledge that can be fed back to direct future lesion marking processes.

Lesion marking refers to a process in which a marking is created with respect to a lesion contained in a patient study such as an image taken from an organ of a patient. A marking may correspond to any representation of an indication. For example, it may correspond to an arrow pointing at a location in an image where a lesion may be present. It may also correspond to a drawing that represents the boundary of a lesion. It may also correspond to a bounding box in which a lesion is present.

Figure 1:
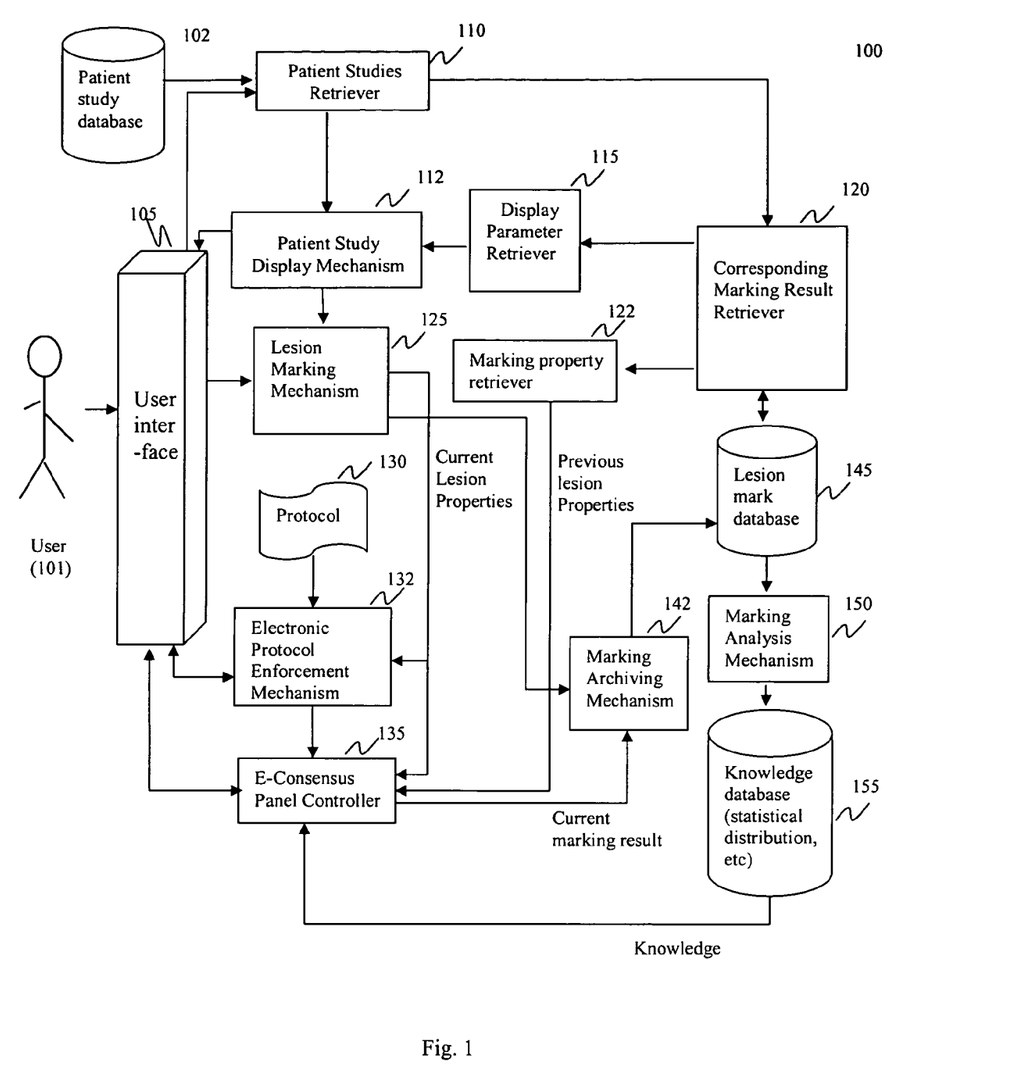
FIG. 1 depicts an exemplary construct of a system facilitating lesion marking with reduced intra and inter observer inconsistencies, according to an embodiment of the present invention.

FIG. 1 depicts an exemplary construct of a system 100 facilitating lesion marking with reduced intra and inter-observer inconsistencies, according to an embodiment of the present invention. The system 100 comprises, in part, a user interface 105, a patient study display mechanism 112, a lesion marking mechanism 125, an electronic protocol enforcement mechanism 132, an electronic consensus panel controller 135, and a marking analysis mechanism 150. In its operation, a user 101 may interact with the system 100 via the user interface 105. The user 101 may initiate a lesion marking process by providing some information related to a patient study. For example, the user 101 may provide a patient ID and a study ID when initiating a lesion marking process for an underlying patient study. The user interface 105, upon receiving user provided information, may forward such information to a patient study retriever 110, which may subsequently obtain the patient study from a patient study database 102. Such retrieved patient study is then forwarded to the patient study display mechanism 112 to be displayed on the user interface 105 for the user's viewing.

During a lesion marking process, the user 101 may interact with the lesion marking mechanism 125 through the user interface 105 to create a lesion marking based on the displayed patient study. For example, the user 101 may make markings or draw on a display screen where the user interface 105 is rendered. Upon receiving the marking coordinates drawn by the user 101 from the user interface 105, the lesion marking mechanism 125 may perform real time detection and quantification of the marked lesion based on the marking received. Measures may be made with respect to the lesion marked and such measures may then be displayed on the user interface 105 so that the user 101 can observe the outcome of the marking created. The user 101 may activate intelligent and interactive lesion analysis tools contained in the lesion marking mechanism 125 to assist marking, for example, suspicious regions in an image as lesion areas. Tools, such as real-time 3D visualization, real-time lesion quantification, and interactive control may be utilized to aid the lesion marking process. In addition, qualitative and/or quantitative properties computed with respect to a marked lesion may be generated. Such lesion properties may be used by the electronic protocol enforcement mechanism 132 to ensure that the created marking complies with a protocol 130 for quality control. In some embodiments, a warning may be issued, if the lesion properties are not consistent with those defined in the protocol 130.

In some embodiments, when a patient study is loaded for lesion marking, a corresponding marking result retriever 120 may automatically search, in a lesion mark database 145, for any previous lesion marking records associated with the same study. Such recorded information related to a previous marking may be used in a current lesion marking process to minimize the inconsistency that may arise under different situations. For example, viewing parameters of a previous lesion marking process may be extracted, by a display parameter retriever 115, and used to reproduce a viewing environment applicable to a previous marking process in which the previous marking is created. In some embodiments, an action sequence taken in the previous lesion marking process may also be recorded and retrieved in a future marking process so that it can be used to replay the entire lesion marking decision process or a portion thereof with respect to any particular lesion.

Features associated with each previous marking may also be utilized for quality assurance purposes. For instance, the location and size of a lesion derived based on a previous lesion marking may be used to compare with similar measures derived from a lesion marking created in a current marking process. A marking property retriever 122 may extract information related to a previously generated lesion marking and forward such information to the electronic consensus panel controller 135 for consistency checking and quality control. Characterization properties of a previously created marking may be compared with that of a lesion of a current marking through the electronic consensus panel controller 135. The e-consensus panel controller 135 may present different sets of features associated with different markings on an electronic consensus panel so that the user 101 can compare the features and examine the discrepancy. In some embodiments, a confirmation of consistency or a warning of inconsistency message may be generated and displayed to the user 101. The user 101 may be given an opportunity to interactively respond to such displayed conclusion.

Through the e-consensus panel, the user 101 may be provided with an opportunity to interactively derive an improved lesion marking in light of the discrepancy between the two markings. Derivation of an improved marking may be based on all available information associated with both the current and the previous marking processes. The user 101 may choose to accept or reject the current marking or specify how the two markings may be combined/fused to generate an integrated marking. When a choice is made, the chosen marking may be treated as a consensus marking. Information related to the accepted marking such as viewing settings, action sequences, and lesion properties, may be automatically archived (if not already done), via a marking archiving mechanism 142, into the lesion mark database 145.

In some embodiments, information stored in the lesion mark database 145 may be analyzed by a marking analysis mechanism 150. Various analyses may be performed to derive statistics and to develop knowledge associated with lesion marking. For example, a benchmark study may be performed based on information stored in the lesion mark database 145 to derive a correlation between different categories of factors (e.g., imaging parameters) and the quality of generated markings. As another example, analysis may be performed based on stored lesion markings to determine typical characterization of different types of lesions (e.g., average size of liver cancer) with respect to, e.g., different race/age groups or stage of the underlying diseases. The analysis may also be carried out with respect to, for example, individual physicians or a group of physicians. From such analyses, collective or individual marking behavior and/or performance may be identified. For example, a specific physician may tend to make a certain kind of mistakes. This behavior pattern may be used in future lesion marking processes, for example, when the specific physician participates or in selection of qualified physicians for marking purposes.

In some embodiments, such derived statistics and knowledge may be stored in a knowledge database 155 and/or can be fed back to the e-consensus panel controller 135 and utilized in a lesion marking process. Details related to various components of the system 100 are discussed below with reference to FIGS. 2-4.

Figure 2:
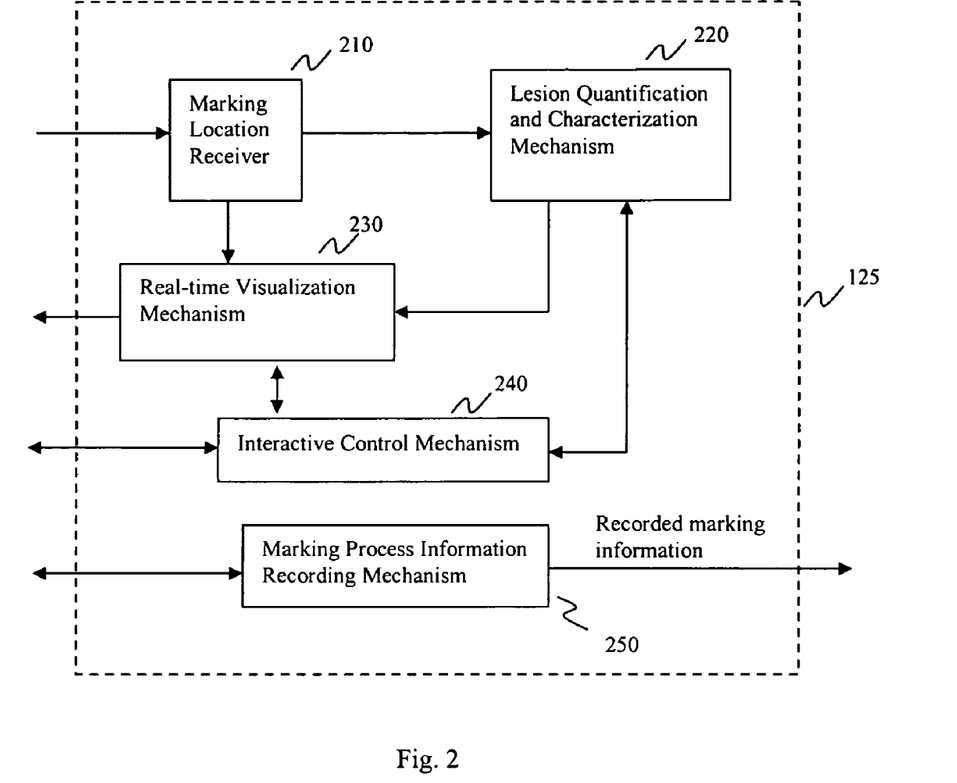
FIG. 2 depicts an exemplary internal structure of a lesion marking mechanism, according to an embodiment of the present invention.

FIG. 2 depicts an exemplary internal structure of the lesion marking mechanism 125, according to an embodiment of the present invention. The exemplary lesion marking mechanism 125 comprises a marking location receiver 210, a lesion characterization mechanism 220, a real-time visualization mechanism 230, an interactive control mechanism 240, and a marking process information recording mechanism 250. In its operation, when information related to the location of a marking is received, the marking location receiver 210 may forward such information to both the lesion characterization mechanism 220 and the real-time visualization mechanism 230. The lesion characterization mechanism 220 may include various processing components that are capable of, for example, detecting/segmenting a lesion given the received marking location and extracting relevant features of the detected lesion. The real time visualization mechanism 230 may visualize the segmented lesion (e.g., boundary) and/or features associated with the lesion near the given location of the marking.

The lesion characterization mechanism 220 may be configured to be capable of various operations that can be applied to a given patient study based on a marked lesion position (e.g., a marking). For example, the lesion characterization mechanism 220 may provide the capability of automated or interactive image segmentation. In some embodiments, a given lesion marking position may provide a parameter for a segmentation process. For instance, a marking may be placed at the interior of a lesion and an automated region based segmentation process may use the marking as a seed to continue a region growing process until reaching the boundary of the lesion. In different embodiments, an interactive segmentation process may also be applied, e.g., within a marking that is a bounding box of a lesion, that allows a user to, for example, specify a number of points along the boundary of a lesion and then an automated interpolation process is applied to derive an optimized lesion boundary. In some embodiments, an automated segmentation may also be coupled with an interactive segmentation process. For example, a lesion boundary generated by an automated segmentation routine may be interactively adjusted via an interactive segmentation algorithm by allowing a user to drag and move a portion of the automatically segmented boundary or by adjusting some governing parameters of the segmentation procedure.

In some embodiments, the lesion characterization mechanism 220 may also be capable of provide quantification of a lesion. Quantitative measurements may include, but are not limited to, the size or volume of the lesion, calcification pattern, attachment pattern with respect to other anatomies, a measure indicating how likely it is that a lesion exists, and a measure indicating how likely it is that the detected lesion is malignant.

The interactive control mechanism 240 may facilitate any interactions between the user 101 and the lesion marking mechanism 125. For example, the user 101 may interactively change or refine the lesion boundary. In this case, the interactive control mechanism 240 may facilitate such interactions by activating the lesion characterization mechanism 220 and the real time visualization mechanism 230 to accordingly effectuate the user's intention. For instance, if the user 101 changes a lesion contour segmented by the lesion characterization mechanism 220, such changes, when received by the interactive control mechanism 240, are forwarded to the lesion characterization mechanism 220 so that features with respect to the revised lesion may be derived. Such recomputed features, together with the revised lesion boundary, may also be forwarded to the real time visualization mechanism 230 so that the lesion boundary as well as newly derived features may be re-displayed to the user 101.

In some embodiments, the interactive control mechanism 240 may be configured to provide a user the ability to enter annotations. For example, a user may be provided with the means to select a lesion associated with a marking and to enter relevant comments and/or notes associated with the marking and/or lesion. In some embodiments, the interactive control mechanism 240 may also be configured to provide a user the ability to query. For example, a user may be allowed to query against a database. Such a query may be formulated based on different criteria such as a type of lesion, a size measure, a shape, an attachment pattern, or some statistics such as an average intensity level within a lesion or an average texture measure with respect to a particular type of lesion. The interactive control mechanism 240 may facilitate communications between a user and a database where a query is sent, receive the query result, and display the result to the user. Such a query may be issued against the knowledge database 155 or any other local or remote databases.

The marking process information recording mechanism 250 records different types of information associated with the lesion marking process. Such information, when a marking is accepted, may be sent to the marking archiving mechanism 142 to be stored together with the marking itself. Information related to activities that occurred during a marking process may provide some insight as to the rationale or reasoning that a user relies on to mark a suspicious region. To maximize the consistency between/among different markings, it may be helpful to provide information reflecting such activities. In addition, such recorded information may assist one in reaching an understanding of particular intra- and inter-observer discrepancies.

In some embodiments, information related to marking decision making may include parameter selections made and/or operations performed during a marking process. Conditions under which an image or a specific portion of an image are visually examined may influence a user's decision in marking and characterizing a lesion. To develop consistent marking with respect to the same lesion, it may be helpful to present an image under the same conditions as when a previous marking for the same lesion was created, for instance, viewing parameters a user selects with respect to each region for which a marking and its underlying lesion characterization is performed. Such viewing parameters may include a window level for image display, a magnification factor applied, a viewing mode (e.g., original image, Maximum Intensity Projection (MIP), or volume rendering), and/or a specific orientation (e.g., axial, sagittal, or coronal).

In some embodiments, information about a sequence of actions/operations taken with respect to a lesion marking process may be recorded. For example, a user may use specific interactive segmentation tools coupled with some particular volume rendering tools to examine a region suspected to contain a lesion. Such actions/operations undertaken by a user may influence how and why the user reaches a conclusion associated with a marking and may be recorded with respect to each of the marking positions.

In some embodiments, such recorded action sequences, when coupled with the recorded corresponding viewing parameters, may enable a replay of the entire user interaction process. Such replay may be effectuated via movie clips or by reproducing a previous process by applying a recorded action sequence to a data set. The former usually has a higher space requirement and no future interaction is possible. The latter often yields savings in terms of space. In some embodiments, the latter makes it possible to allow a user to participate in the process in which a recorded action sequence is being reproduced. For example, a previous interactive segmentation process to delineate a lesion boundary may be reproduced base on the recorded tools used and the threshold parameters set in such tools. A user in a different marking process may be allowed to adjust, during the replay, the threshold parameters for the tools used in the previous interactive segmentation process and observe the impact of such threshold change on the segmentation results.

Figure 3:
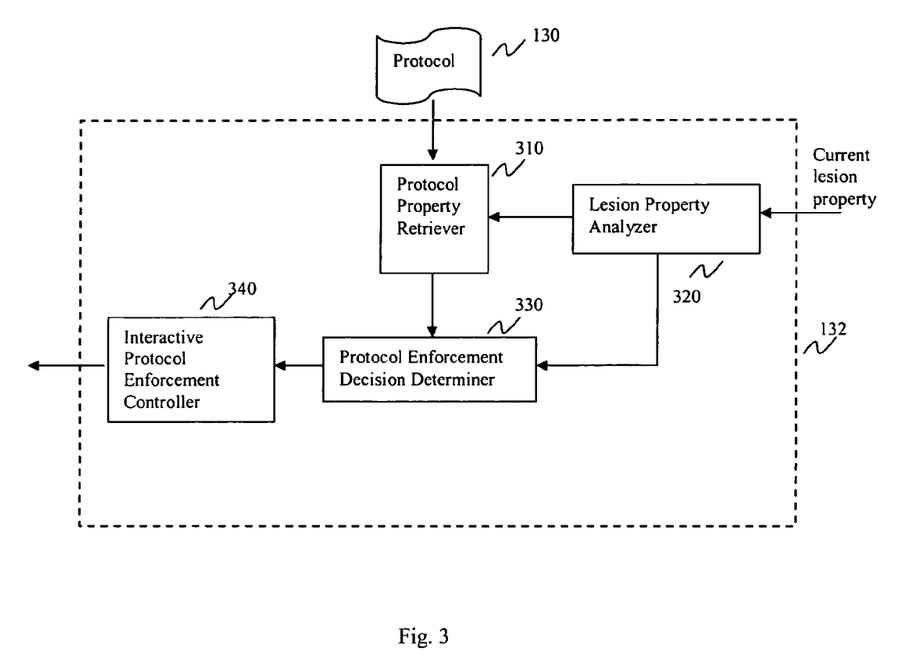
FIG. 3 depicts an exemplary internal structure of an electronic protocol enforcement mechanism, according to an embodiment of the present invention.

FIG. 3 depicts an exemplary internal structure of the electronic protocol enforcement mechanism 132, according to an embodiment of the present invention. In this exemplary construct, the electronic protocol enforcement mechanism 132 comprises a lesion property analyzer 320, a protocol property retriever 310, a protocol enforcement decision determiner 330, and an interactive protocol enforcement controller 340. In its operation, the lesion property analyzer 320 analyzes features characterizing a lesion from, for example, the lesion marking mechanism 125. The features may be extracted from the lesion that is detected/segmented based on a marking created by the user 101. The lesion property analyzer 320 may identify features that are relevant to the protocol. If such features are present, the lesion property analyzer 320 may activate the protocol property retriever 310 to obtain corresponding features required by the protocol from the stored protocol 130. In some embodiments, features present in both the received feature set and the protocol are compared and a decision as to whether the lesion characterized by the received features is in compliance with the protocol 130 is made by the protocol enforcement decision determiner 330. Based on such a decision, the interactive protocol enforcement controller 340 may carry out the enforcement decision interactively with the user 101.

The protocol 130 may refer to one or more criteria to be complied with when a user creates a lesion marking. One of the important factors attributable to reading inconsistencies may be that radiologists often employ different criteria when they create markings. Although sometimes radiologists may agree to use a protocol, when there is no effective mechanism to enforce the protocol in the process of creating markings, the markings generated are still subject to both inconsistency, including both intra-observer inconsistency and inter-observer inconsistency. The former refers to the situation where lesion markings created by a radiologist at different times are inconsistent. The latter refers to the situation where lesion markings created by different radiologists are inconsistent. In the invention described herein, the protocol 130 is electronically enforced during the process when a radiologist creates a lesion marking to reduce both intra-observer and inter-observer inconsistencies.

The protocol 130 may be established in different ways and may be updated over time. In some embodiments, the protocol 130 may be in the form of an electronic file, containing descriptions of criteria to be satisfied during creating a lesion marking. A template file may be used to formulate the criteria for marking a lesion. Such a template may include one or more parts, including, for example, a general description and/or a category matrix. A general description may define what is to be marked such as the type of abnormality to be marked, a feature description such as a size range of the lesion to be marked, whether it should be calcified, and/or whether other abnormalities other than a lesion form should be marked. A category matrix may describe detailed features for lesions to be marked, including, but not limited to, shape, malignancy likelihood, status regarding solidness of a lesion, calcification distribution, a form of connection to other structures, subtlety, and/or treatment categories.

Criteria so defined in the protocol 130 may be enforced against features extracted from a lesion segmented based on a marking. For example, when the measured size of a lesion falls out of the range specified in the protocol, the underlying marking may be considered inconsistent or invalid. Such enforcement decision may be communicated to the user 101 so that, for example, the user 101 may re-examine the patient study and interactively reach a decision as to the validity of the marking.

The protocol 130 may include some criteria that may not be as precisely quantifiable, which may leave room for ambiguities. In some embodiments, the protocol 130 may be enforced in a different mode of operation through a test reading procedure. During a test reading procedure, pre-selected sample patient studies, which may contain both abnormalities that are easily missed and ones that are often over-marked (i.e. cases that should not be marked but are often mistakenly marked by radiologists), may be used to test a user by requesting the user to create a marking. The test marking result may then be compared with corresponding element(s) of the protocol 130 as to whether the marking created by the user is consistent with the protocol 130. The test reading procedure may be viewed as a process to train a user to avoid markings that are not consistent with the protocol 130. In some embodiments, the protocol 130 may include links to such testing samples and such links may be activated when a marking generated by the user 101 is not consistent with the ground truth of the sample images of that category. Therefore, the test reading procedure may serve as a means to inform and educate a user as to the requirements that the protocol 130 intends to enforce.

Figure 4:
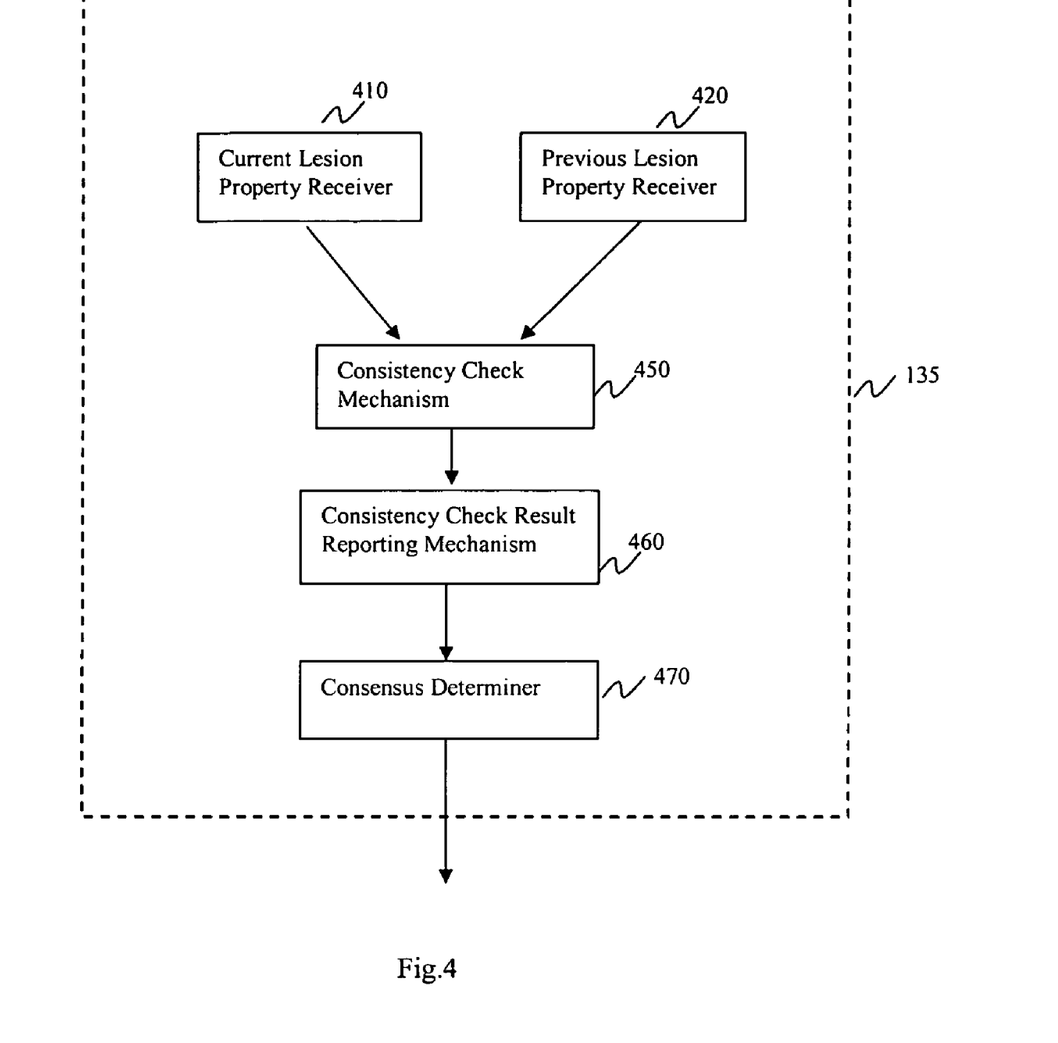
FIG. 4 depicts an exemplary internal structure of an electronic consensus panel controller, according to an embodiment of the present invention.

A different aspect of reducing intra-observer and inter-observer inconsistency in addition to electronic protocol enforcement relates to consistency checking performed when multiple markings are present for a single lesion. FIG. 4 depicts an exemplary internal structure of the electronic consensus panel controller 135, according to an embodiment of the present invention. The electronic consensus panel controller 135 comprises a pair of lesion property receivers with one for a current marking and the other set for a previous marking (410, 420), an automatic consistency check mechanism 450, a consistency check result reporting mechanism 460, and a consensus determiner 470.

When multiple markings are made for the same lesion, the e-consensus panel controller 135 may check the consistency of the different markings and interact with the user 101 to attempt to reach a consensus. The current lesion property retriever 410 obtains features characterizing a marking created in the current marking process and the previous lesion property retriever 420 obtains features characterizing a previous marking. Both sets of features are forwarded to the consistency check mechanism 450 where the two sets of features may be compared and analyzed in terms of marking inconsistency. The consistency check result reporting mechanism 460 may receive the comparison result and report the same to the user. When a discrepancy exists, the consensus determiner 470 may interact with the user in order to resolve the discrepancy and to reach a consensus.

In some embodiments, both the current and the previous markings may be displayed side-by-side on a display screen for visual comparison and inspection. Inconsistent measurements may also be presented to the user for examination. Furthermore, the action sequences of the two marks may be retrieved. The user may be given the option to reproduce a previous marking process based on the action sequences. Such reproduction may be carried out fully or partially, focusing on the portion where the inconsistency may have occurred.

In some embodiments, the consensus determiner 470 may conduct different interactive processes for intra-observer and inter-observer inconsistencies. For intra-observer inconsistency, a side-by-side quantitative comparison may be performed. If a previous marking is not marked at the current location, a user may be prompted to check the previous marking using recorded viewing parameters and action sequences. If the user decides that both the previous marking and the current marking are acceptable, the user may be given the option of merging the two markings, e.g., by transferring the previous marking to the current reading. If the user determines that the previous marking should not be accepted in the current reading, then the current marking may be treated as a consensus marking.

An inter-observer inconsistency often corresponds to a situation where a patient study is marked on different systems. In those situations, previous marking results may be imported through means such as FTP, web download, or email via network connections such as the Internet, LAN, WAN, etc. There may be more than one previous marking. In some embodiments, the most recent previous marking may be considered to be an integration or consensus of all previous markings. This is a progressive mode of reaching a consensus among different markings. In some situations, there may not be a consensus reached among multiple markings. In this case, to ensure consistency, each marking may be sent to a third party for a benchmark analysis or to other marking creators for inconsistency checking.

There are scenarios where multiple medical centers read the same set of patient studies. Marking inconsistencies among different medical centers may be analyzed at a statistical level instead of at an individual level. For example, comparison of different markings created by different centers may be carried out based on statistics collected at each medical center. Cross-center inconsistency may then be accordingly defined based on such statistics. For example, if a degree of inconsistency is defined based on a difference between corresponding likelihood attributes of two markings, then each medical center may compute a series of statistics such as the percentage of consistent markings, an average degree of inconsistency, a variance of the degree of inconsistency, the percentage distribution of markers with a certain degree of inconsistency, the same statistical measures as above but for consistencies of characteristics of markings. Such statistical measures from different medical centers may then be used to assess levels of inconsistency/consistency across different medical centers.

Figure 5:
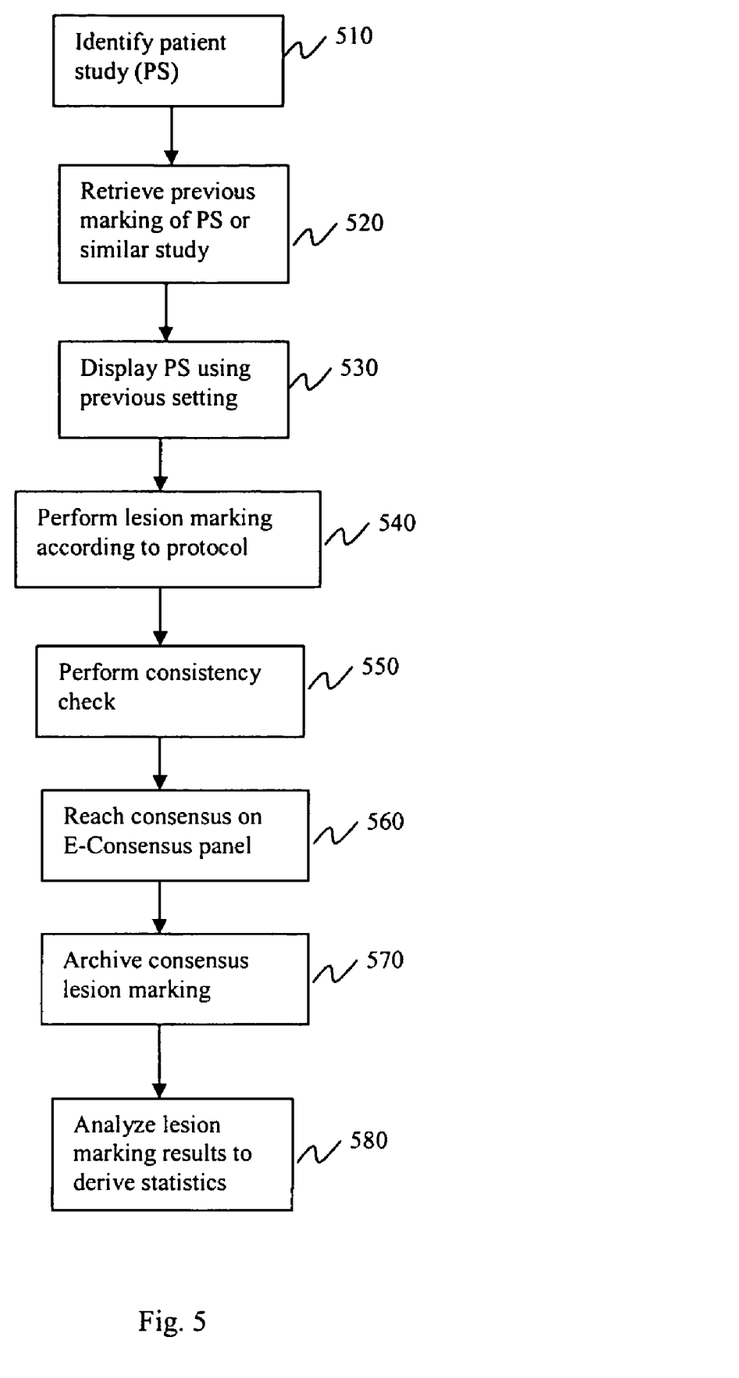
FIG. 5 is a flowchart of an exemplary process for lesion marking with reduced intra and inter observer inconsistencies, according to an embodiment of the present invention.

Flowcharts of different exemplary processes related to the system 100 and different components thereof as described herein are discussed with reference to FIGS. 5-8. FIG. 5 is a flowchart of an exemplary process for lesion marking to reduce intra- and inter-observer inconsistencies, according to an embodiment of the present invention. A patient study for which lesion marking is to be performed is first identified at 510. Based on the patient study information, marking(s), if any, that are created previously for the same or similar patient study are retrieved at 520. Such retrieval may include both the markings as well as any information associated with the previous markings such as features characterizing the markings and parameters used to creating the previous markings. When such previous markings exist, the patient study is displayed, at 530, based on viewing parameters employed in a lesion marking process in which the previous marking was created.

An interactive lesion marking process is conducted, at 540, in a manner that is in compliance with the electronically enforced protocol 130. With respect to each marking so created, a consistency check is performed, at 550, between a marking created and one or more previous markings. When inconsistency exists, a consensus is reached at 560 that gives rise to a marking that can be used in a future lesion marking process as a consensus marking. Such a consensus marking is then archived, at 570, together with information associated with it such as viewing parameters and action sequences, etc. The archived markings stored in a database may be analyzed, at 580, to obtain various statistics/knowledge. Details related to interactive lesion marking, consistency checks, and electronic consensus marking are discussed with respect to FIGS. 6-8.

Figure 6:
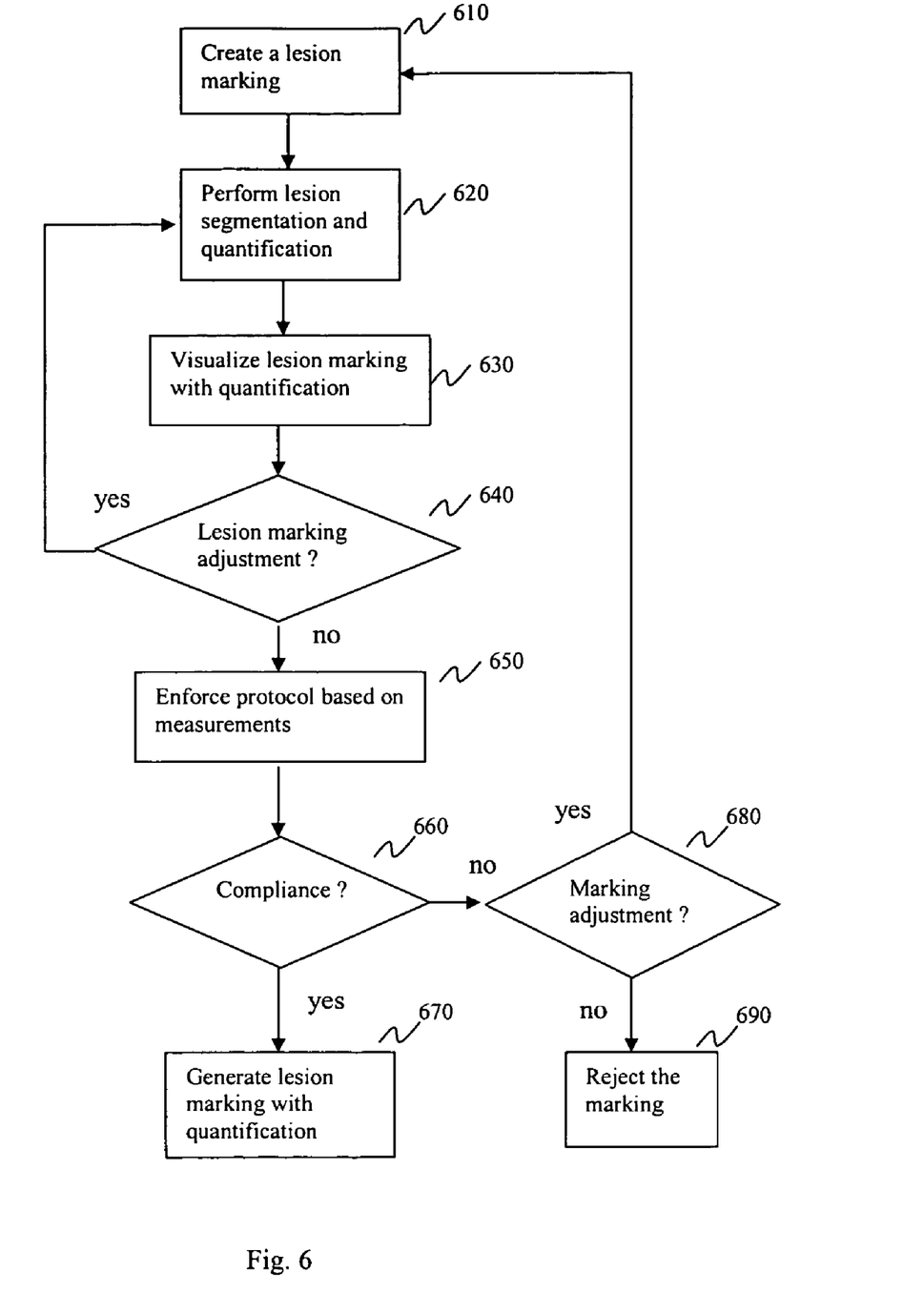
FIG. 6 is a flowchart of an exemplary process for interactive lesion marking, according to an embodiment of the present invention.

FIG. 6 is a flowchart of an exemplary process for interactive lesion marking, according to an embodiment of the present invention. During an interactive process of lesion marking, when a signal signifying a lesion marking is created, at 610, certain processing such as segmentation and/or feature extraction is applied, at 620, to identify the underlying lesion and a characterization thereof. The processing result may be visualized, at 630, and used to assess, at 640, whether criteria defined in the protocol 130 are satisfied. If the marking created does not comply with the protocol 130, determined at 660 and if no adjustment to the marking is to be made, determined at 680, the marking is rejected, at 690, for failing to comply with the protocol 130. When an adjustment is to be made, the process returns to either an interactive process to make an adjustment to the marking itself at 610 or a process of lesion characterization at 620 (not shown). When the marking and lesion characterization thereof satisfy the protocol 130, a user may still decide to make some adjustment to the marking, determined at 680. Similarly, the adjustment may be made at either 610 or 620 (not shown). Any adjusted marking and lesion characterization thereof are subject to electronic enforcement of the protocol 130. When no adjustment is to be made to a valid marking (i.e., that is in compliance with the protocol 130), the marking is generated together with relevant parameters at 670.

Figure 7:
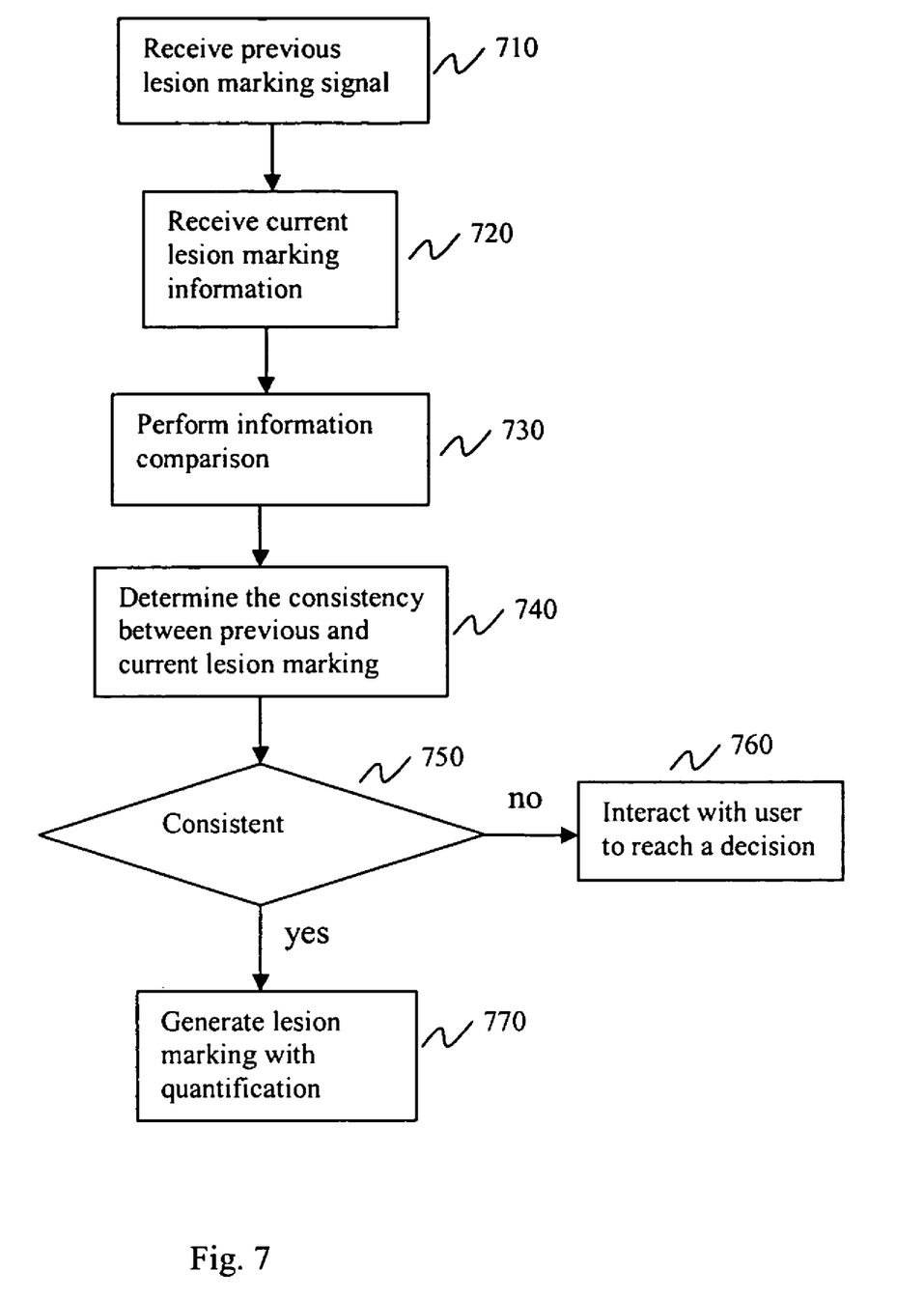
FIG. 7 is a flowchart of an exemplary process for lesion marking quality assurance based on a consistency check, according to an embodiment of the present invention.

FIG. 7 is a flowchart of an exemplary process for lesion marking quality assurance based on consistency checking, according to an embodiment of the present invention. Information related to a previous and a current marking is received at 710 and 720, respectively. Such received information is compared at 730 for consistency. A determination is made, at 740, as to whether the previous marking and the current marking are consistent. If they are consistent, determined at 750, a lesion marking is created together with information associated with the marking such as viewing parameters, action sequences, an underlying lesion and characterization thereof. When the current marking is inconsistent with the previous marking, an interactive process is initiated, at 760, in order to reach a consensus as to how to resolve the inconsistency.

Figure 8:
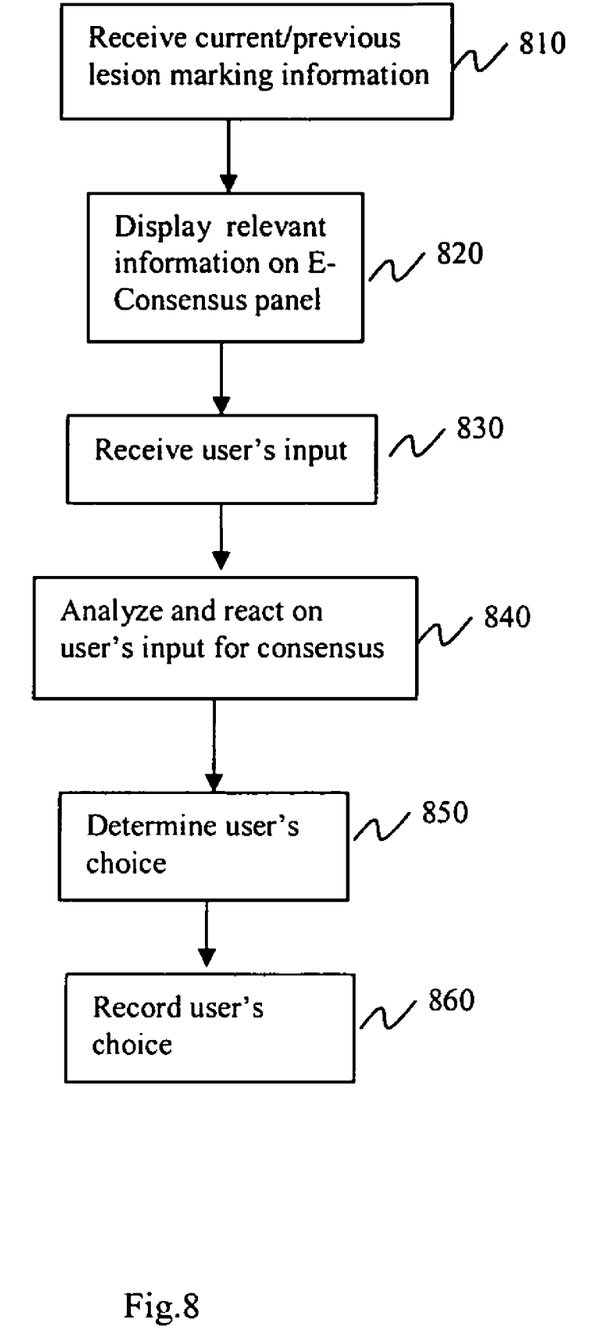
FIG. 8 is a flowchart of an exemplary process for obtaining a consensus lesion marking, according to an embodiment of the present invention.

FIG. 8 is a flowchart of an exemplary process for interactively obtaining a consensus lesion marking, according to an embodiment of the present invention. Information related to a current and one or more previous markings are received, at 810, and displayed, e.g., side-by-side, on an electronic consensus panel at 820. In the interactive process, a user may enter information related to a consensus marking. When such input is received, at 830, it is analyzed at 840. A choice according to the user's input is determined at 850 based on the analysis and a consensus marking is recorded at 860.

While the invention has been described with reference to the certain illustrated embodiments, the words that have been used herein are words of description, rather than words of limitation. Changes may be made, within the purview of the appended claims, without departing from the scope and spirit of the invention in its aspects. Although the invention has been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

What is claimed is:

1. A method for quality assurance in diagnostic imaging, comprising:
    deploying a quality assurance protocol to be used to minimize inconsistency in creating, by a plurality of different creators or by a same creator at different times, a current marking of an object in a displayed patient study with respect to a second marking which includes a marking previously created with respect to the same object in the patient study or a marking previously created with respect to a similar patient study;
    electronically enforcing the quality assurance protocol while creating the current marking with respect to the object in the displayed patient study by
    interacting with a creator of the current marking to obtain the current marking;
    comparing the current marking with the second marking, made by a different creator or by a same creator at a different time, based on a criterion predefined by the quality assurance protocol, and generating a warning to the creator of the current marking if there is inconsistency between the current marking and the second marking with respect to the predefined criterion.

2. The method according to claim 1, wherein the patient study is displayed by:

determining whether the second marking exists;

retrieving the second marking if the second marking exists; and presenting the patient study, if the second marking exists, in an environment consistent with that in which the second marking is created.

3. The method according to claim 2, wherein the second marking is retrieved remotely.

4. The method according to claim 2, wherein the displayed patient study is presented based on one or more parameters used when the second marking is created.

5. The method according to claim 4, wherein the one or more parameters include at least one of a parameter and an action sequence recorded based on one or more operations carried out when the second marking is created.

6. The method according to claim 4, wherein the marking marks an object of interest.

7. The method according to claim 6, wherein the one or more features characterize the marking or the marked object.

8. The method according to claim 6, wherein the marked object is a lesion.

9. The method according to claim 1, wherein the current marking is created via an interactive process and the protocol is electronically enforced during the interactive process.

10. The method according to claim 1, wherein the protocol specifies at least one criterion to be evaluated and enforced when the current marking is created.

11. The method according to claim 10, wherein the at least one criterion includes a quantitative criterion.

12. The method according to claim 11, wherein the quantitative criterion includes a range for an acceptable size of an object associated with the marking.

13. The method according to claim 10, wherein the at least one criterion includes a qualitative criterion.

14. The method according to claim 13, wherein the qualitative criterion includes an assessment made with respect to a test marking created during a test reading session as to whether a test marking is consistent with ground truth established as a part of the protocol.

15. The method according to claim 10, wherein the current marking is created in a process, comprising:

receiving a signal corresponding to the current marking;

performing object detection and quantification based on the current marking to produce the one or more features associated with the detected object;

electronically enforcing the protocol based on the one or more features with respect to the at least one criterion specified by the protocol;

making an adjustment with respect to the current marking or the object detection until the at least one criteria of the protocol is satisfied, yielding the current marking; and recording at least one of the current marking, its associated one or more features, and/or one or more parameters associated with the process of generating the current marking.

16. The method according to claim 15, wherein the one or more parameters include at least one of a parameter used in creating the current marking and an action sequence related to one or more operations performed during creating the current marking.

17. The method according to claim 7, wherein the one or more features characterizing the current marking include at least one of a qualitative feature and a quantitative feature.

18. The method according to claim 17, wherein the quantitative feature includes a size of an object marked by the current marking.

19. The method according to claim 1, wherein said assessing includes detecting inconsistency and/or consistency between the current marking and the second marking.

20. The method according to claim 19, wherein said detecting the inconsistency and/or consistency comprises:

comparing the current marking with the second marking; and determining whether the current marking and the second marking are inconsistent.

21. The method according to claim 20, wherein said comparing includes visual comparison of the current marking and the second marking.

22. The method according to claim 20, wherein said comparing includes evaluating a discrepancy between the one or more features characterizing the current marking and one or more features that characterize the second marking.

23. The method according to claim 20, further comprising reporting an inconsistency when said determining concludes the inconsistency.

24. The method according to claim 19, wherein the inconsistency includes inter-observer inconsistency, where the current marking and the second marking are created by different creators.

25. The method according to claim 19, wherein the inconsistency includes intra-observer inconsistency, where the current marking and the second marking are created by a same creator.

26. The method according to claim 19, wherein the second marking is used to assist creating the current marking.

27. The method according to claim 19, further comprising determining a consensus marking based on the current marking and the second marking.

28. The method according to claim 19, further comprising archiving the current marking in a marking database when said assessing determines that the current marking is valid.

29. The method according to claim 28, further comprising analyzing information in the marking database to derive statistics.

30. The method according to claim 29, wherein the statistics characterize intra-observer and/or inter-observer inconsistency and/or consistency.

31. The method according to claim 29, wherein the statistics provides characterization with respect to object type.

32. The method according to claim 29, wherein the statistics provides characterization with respect to patient type.

33. A method for quality assurance in diagnostic imaging, comprising:

creating a current marking of an object in a patient study;

generating one or more features based on the current marking, wherein the one or more features are predefined in a quality assurance protocol; and assessing quality of the current marking by electronically enforcing the quality assurance protocol by detecting inconsistency between the current marking and a second marking, created previously by a different creator or by a same creator at a different time, based on the one or more features associated with the current marking and one or more features associated with the second marking, wherein the second marking includes a marking previously created with respect to the same object in the patient study or a marking previously created with respect to a similar patient study.

34. The method according to claim 33, wherein said assessing comprises:
comparing the one or more features of the current marking with the one or more features of the second marking; and
determining whether the inconsistency exists between the current marking and the second marking.

35. The method according to claim 34, wherein the inconsistency includes an inter-observer inconsistency, where the current marking and the second marking are created by different creators.

36. The method according to claim 34, wherein the inconsistency includes an intra-observer inconsistency, where the current marking and the second marking are created by a same creator at different times.

37. The method according to claim 33, further comprising generating a consensus marking based on the current marking and the second marking.

38. The method according to claim 37, further comprising archiving the consensus marking in a marking database.

39. The method according to claim 38, further comprising analyzing information contained in the marking database to derive statistics characterizing inconsistency patterns across markings stored in the marking database.

40. The method according to claim 38, wherein the statistics characterize intra-observer and/or inter-observer inconsistency and/or consistency.

41. The method according to claim 38, wherein the statistics characterize cross-locale inconsistency and/or consistency, where different markings based on which the inconsistency and/or consistency is assessed are created at different locales.

42. A method for quality assurance in diagnostic imaging, comprising:
creating a current marking of an object in a patient study, by enforcing electronically a quality assurance protocol, with respect to a second marking made previously by a different creator or by a same creator at a different time;
generating one or more features, predefined in accordance with the quality assurance protocol, based on the current marking; and
generating a consensus marking from the current marking and the second marking based on the one or more features associated with the current marking and one or more features associated with the second marking.

43. The method according to claim 42, wherein the second marking is created previously with respect to the object in the patient study or an object in a similar study.

44. The method according to claim 42, wherein said generating the consensus marking comprises:
displaying information related to the current marking and the second marking;
receiving an input indicating a decision related to a consensus made based on the information related to the current marking and the second marking; and
creating the consensus marking based on the information and the input.

45. The method according to claim 42, wherein the information relates to a measure characterizing an inconsistency between the current marking and the second marking.

46. A system for quality assurance in diagnostic imaging, comprising:
a quality assurance protocol to be used to minimize inconsistency in creating, by a plurality of different creators or by a same creator at different times via a marking mechanism, a current marking of an object in a displayed patient study with respect to a second marking which includes a marking previously created with respect to the same object in the patient study or a marking previously created with respect to a similar patient study;
an electronic protocol enforcement mechanism configured to electronically enforce the quality assurance protocol while creating the current marking of the object in a patient study by
interacting with a creator of the current marking to obtain the current marking;
comparing the current marking with the second marking, made by a different creator or by a same creator at a different time, based on a criterion predefined by the quality assurance protocol, and
generating a warning to the creator of the current marking if there is inconsistency between the current marking and the second marking with respect to the predefined criterion; and
a quality assurance mechanism configured to assess quality of the current marking based on one or more features characterizing the current marking in accordance with the quality assurance protocol.

47. The system according to claim 46, wherein the quality assurance mechanism is capable of assessing inconsistency between the current marking and the second marking previously created, wherein the inconsistency is an indication of the quality of the marking.

48. The system according to claim 47, wherein the marking mechanism is capable of facilitating creation of a consensus marking based on the current marking and the second marking.

49. The system according to claim 46, further comprising an marking information analysis mechanism configured to analyze information related to one or more markings to derive statistics relating to quality of the one or more markings.

50. A system for quality control in diagnostic imaging, comprising:
a marking mechanism configured to facilitate creation of a current marking associated with an object in a patient study; and
a quality assurance mechanism configured to evaluate-quality of the current marking in relation to a second marking, created by a different creator or a same creator at a different time, by comparing one or more features characterizing the current marking computed in accordance with one or more criteria predefined by the electronically enforced quality assurance protocol, with one or more features characterizing the second marking, wherein the second marking includes a marking previously created with respect to the same object in the patient study or a marking previously created with respect to a similar patient study.

51. A system for assisted medical diagnosis, comprising:
a marking information receiver configured to receive information related to a plurality of markings created by different creators or a same creator at different times in a consistent manner in accordance with an electronically enforced quality assurance protocol;
a consensus information receiver configured to receive a consensus choice made with respect to the markings and information related to the consensus choice;

an information fusion mechanism configured to combine information related to the markings with information related to the consensus choice to produce combined information;

a consensus marking generation mechanism configured to generate a consensus marking based on the combined information; and a quality assurance mechanism configured to evaluate quality of the consensus marking based on one or more features predefined by the quality assurance protocol and characterizing the consensus marking and one or more features characterizing the markings.

52. The system according to claim 51, wherein the plurality of markings are associated with a patent study.

53. The system according to claim 51, wherein the quality assurance mechanism is capable of assessing an inconsistency between the consensus marking and one or more of the markings.

* * * * *